United States Patent [19]

Yoneyama et al.

[11] Patent Number: 5,182,617
[45] Date of Patent: Jan. 26, 1993

[54] SAMPLE SUPPLY DEVICE AND SAMPLE INSPECTION APPARATUS USING THE DEVICE

[75] Inventors: Yoshito Yoneyama, Kawasaki; Yoshiyuki Toge; Naoki Yuguchi, both of Yokohama, all of Japan

[73] Assignee: Canon Kabushiki Kaisha, Tokyo, Japan

[21] Appl. No.: 545,589

[22] Filed: Jun. 29, 1990

[30] Foreign Application Priority Data

Jul. 20, 1989 [JP] Japan ................................ 1-189728

[51] Int. Cl.⁵ .......................................... G01N 21/05
[52] U.S. Cl. ...................................... 356/440; 356/39; 356/336; 356/410; 137/93; 137/112
[58] Field of Search .................... 356/440, 39, 72, 73, 356/410, 315, 336, 246; 324/71.4; 436/534; 422/67; 137/625 H, 624.13, 624.14, 625.11, 93, 112, 625.18

[56] References Cited

U.S. PATENT DOCUMENTS

| | | | |
|---|---|---|---|
| 3,604,814 | 9/1971 | Skeggs | 356/171 |
| 4,606,631 | 8/1986 | Anno et al. | 356/39 |
| 4,854,838 | 8/1989 | Swain | 137/625.18 |

Primary Examiner—Vincent P. McGraw
Assistant Examiner—LaCharles P. Keesee
Attorney, Agent, or Firm—Fitzpatrick, Cella, Harper & Scinto

[57] ABSTRACT

A sample supply device includes first and second sample supply means for independently receiving respective samples via a common channel and for supplying the samples to an inspection position. The device is controlled so that the second sample supply means performs a sample receiving operation and/or a washing operation with the channel, while the first sample supply means supplies the sample to the inspection position. A sample inspection apparatus inspects the sample at the inspection position principally using an optical method.

32 Claims, 6 Drawing Sheets

SAMPLE SUPPLY DEVICE AND SAMPLE INSPECTION APPARATUS USING THE DEVICE

BACKGROUND OF THE INVENTION

1. Field of the Invention

This invention relates to a sample supply device for supplying a supply unit with a sample, which is used, for example, for a flow cytometer or the like, and also relates to a sample inspection apparatus using the device.

2. Description of the Prior Art

In a conventional sample inspection apparatus, for example, a flow cytometer, a sample, such as blood, humor or the like, is first taken within the flow cytometer and stored therein. Fine particles, such as biological cells or the like, within the sample are individually separated by a sheath flow method within a flow unit having a minute rectangular cross section of about 250 μm × 250 μm in a central portion of flow cell. Laser light is projected upon the flowing fine particles, and scattered light, fluorescence and the like which are thereby produced are subjected to photometry for each particle. The particles are measured at a high speed of 1000–5000 particles per second. A substance to be inspected is analyzed by statistically processing measured data of scattered light and fluorescence obtained about a large number of particles using a computer.

A latex agglutination measuring method has also been known. In this method, a reagent prepared by sensitizing the surfaces of a large number of carrier fine particles, such as latex particles or the like, with monoclonal antibodies is mixed with a sample, such as serum or the like. If there exist desired antigens within the sample, latex particles combine with one another to form aggregates by the combining function of an antigen-antibody reaction. By introducing this reacted liquid into the flow cytometer, and performing measurement, an agglutinated state is discriminated to perform qualitative or quantitative measurement for the desired antigens. This method is specifically described, for example, in U.S. patent application Ser. No. 304,236, filed Jan. 31, 1989.

In this kind of flow cytometer, after measurement for one sample has ended, a washing liquid flows within a flow channel of the apparatus to perform washing. After the washing has ended, another sample is taken and a measurement of the substance to be inspected is repeated in the same manner.

In the conventional measuring apparatus for a substance to be inspected, however, only one sample can be measured at a time. When a plurality of samples are continuously measured, the measurement of the next sample cannot be started until after the measurement of one sample has ended, and washing within the flow unit has ended, as shown in FIG. 5(A). Due to these problems, it is impossible to perform efficient measurement when various kinds of samples are continuously processed.

SUMMARY OF THE INVENTION

It is an object of the present invention to provide an apparatus which can shorten the cycle of measurement for each sample, and which can improve its processing capability when a plurality of samples are continuously inspected.

It is another object of the present invention to improve the processing capability of an apparatus without sacrificing the cost and space-saving property of the apparatus.

In accordance with one aspect of the present invention, a sample supply device comprises a sample receiving channel for receiving a sample from a source, a sample supply channel for supplying the sample to a supply unit and first and second sample storage means for storing predetermined amounts of respective samples. First and second pressurizing means are in communication with the first and second sample storage means, respectively, for extruding and aspirating liquid stored in the storage means. In addition, channel switching means can switch between a first mode and a second mode, with the first mode being a state in which the first sample storage means is connected to the sample supply channel and the second sample storage means is connected to the sample receiving channel, and the second mode is a state in which the first sample storage means is connected to the sample receiving channel and the second sample storage means is connected to the sample supply channel.

In accordance with another aspect of the present invention, a sample supply device includes first and second sample supply means for independently receiving samples via a common sample receiving channel and for supplying a supply unit with the samples, and control means for controlling the supply means so that the second sample supply means can either receive a sample from the sample receiving channel or wash the sample receiving channel while the first sample supply means supplies the supply unit with the sample.

DETAILED DESCRIPTION OF THE PREFERRED EMBODIMENT

Figure 1:
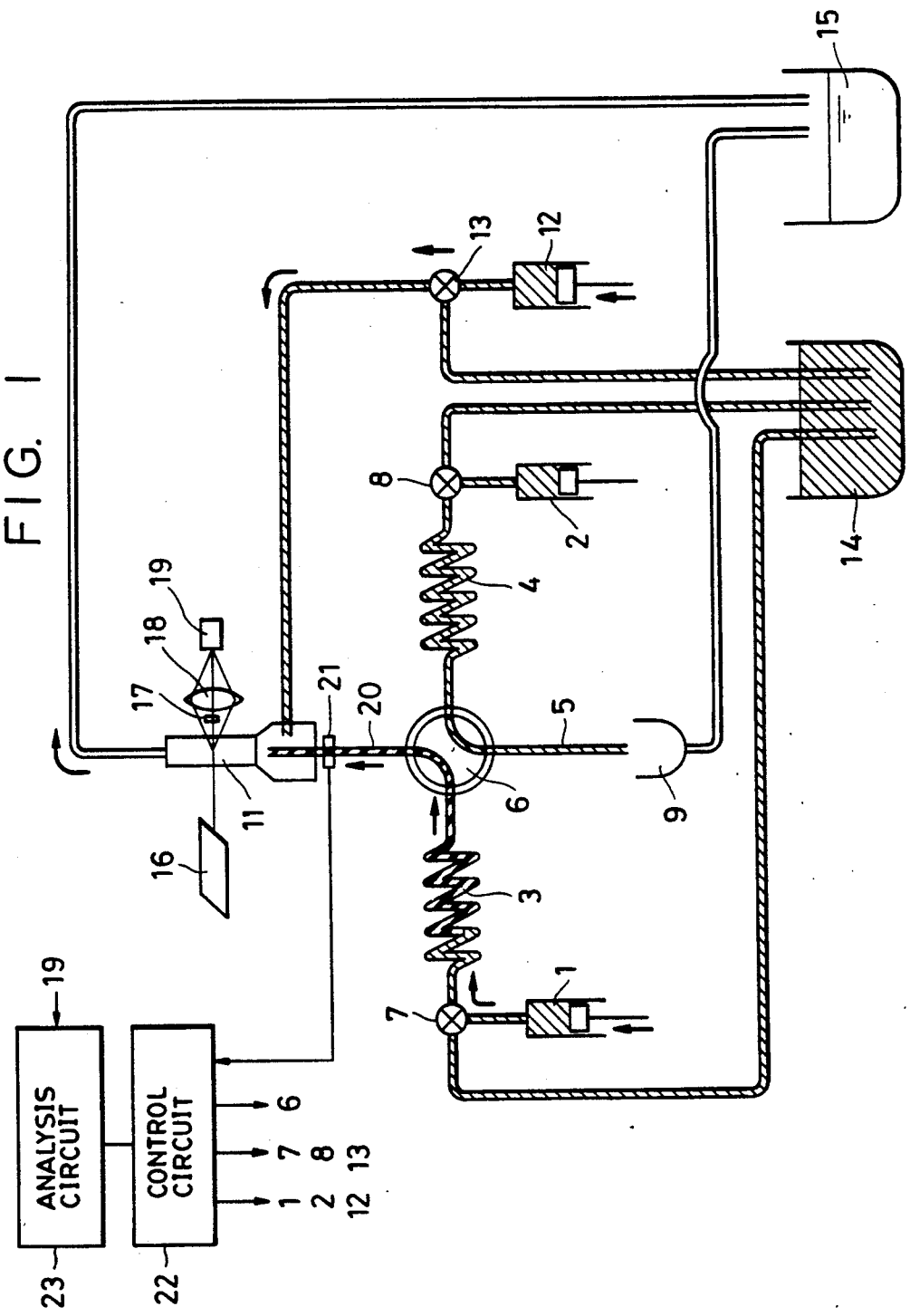
FIG. 1 is a diagram showing the configuration of an embodiment of the present invention.

FIG. 1 is a diagram showing the configuration of a fluid system of an embodiment in which the present invention is applied to a flow cytometer. As samples used in the flow cytometer, a humor, such as blood, urine or the like, a reacted liquid including a latex reagent, a liquid including microorganism, and the like are generally used.

In FIG. 1, independently-controlled first and second syringes perform the extruding and aspirating operation of a liquid. A sheath liquid is filled within each syringe. The syringe 1 is connected to a first sample storage unit 3 and a sheath liquid receptacle 14 via a channel switching valve 7. The switching valve 7 selectively connects the syringe 1 to either one of the sample storage unit 3 and the sheath liquid receptacle 14. Similarly, the channel from the syringe 2 is connected to either one of a second sample storage unit 4 and the sheath liquid receptacle 14 by a switching valve 8. Each of the first and second sample storage units 3 and 4 provide a substantial storage capacity in spite of their small volume by having a spiral-shaped tube, serving as a flow unit, and can store a sample having a volume of about 200 μl. The other end portion of the tube of each of the sample storage units 3 and 4 is connected to a four-way switching valve 6, serving as a channel switching means. Other portions of the four-way switching valve 6 are connected to a sample aspiration or supply tube 5 and a supply tube 20 which extends to a flow cell 11.

A channel from a syringe 12 for supplying the sheath liquid is connected to either one of the flow cell 11 and the sheath liquid receptacle 14 by a switching valve 13. In an initial state, the sheath liquid is aspirated from the sheath liquid receptacle 14 and is filled within the syringe 12. A waste liquid receptacle 15, which receives unnecessary waste liquids, is connected to an outlet of the flow cell 11 and a saucer 9 for the sample aspiration tube 5. The operation of all of the above-described syringes and valves is controlled by a control circuit 22.

An optical sensor unit 21 including a light-emitting device and photosensor, in which the light-emitting device and the photosensor are disposed close to the transparent supply tube 20 and face with each other, can determine whether a substance within the tube is a liquid or air by detecting the optical transmittance of the substance. The output from the optical sensor unit 21 is connected to the control circuit 22.

As an optical system for performing optical measurement by irradiating laser light upon fine particles within a sample flowing through a portion to be inspected, a laser light source 16 irradiates light upon fine particles flowing within the flow cell 11. An Ar+ laser, a He-Ne laser, a semiconductor laser or the like is suitable for the laser light source 16. The light source is, of course, not limited to a laser. A laser beam emitted from the laser light source 16 is projected onto an inspection position within the flow cell 11 via a lens (not shown) or the like. A beam stopper 17 shields a powerful laser light beam which passes the flow cell 11 and goes straight. A lens 18 condenses light scattered in forward or front directions produced by fine particles in the sample. A photodetector 19 performs photometry of the light scattered in forward or front directions condensed by the condensor lens 18. Although not illustrated in FIG. 1, an optical system for performing photometry of light scattered at right angles or side directions and fluorescence produced from a substance to be inspected together with the light scattered in forward or front directions is also provided in a direction perpendicular to the surface of the drawing. Every time each particle of the substance to be inspected passes the position irradiated by the laser, the intensities of the light scattered in forward or front directions, light scattered at right angles or side directions and fluorescence are detected. The outputs of these measurements including the output from the photodetector 19 are taken in an analysis circuit 23, where the calculation of analysis of particles within the samples is performed. Various methods of measurement other than an optical measurement, such as an electrical measurement, an acousto-optical measurement and the like, may also be used.

The operation of the apparatus having the above-described configuration will now be explained. The control of the operation is performed according to commands from the control circuit 22.

In an initial state, an operation is performed to store a predetermined amount and a full amount of the sheath liquid in the syringes 1 and 2, respectively. This operation is performed by aspirating the respective amounts of the sheath liquid into the respective syringes while switching the switching valves 7, 8 and 13 in a position to receive liquid from the sheath liquid receptacle 14. After the aspiration of the sheath liquid has ended, the switching valves are returned to their initial positions.

In FIG. 1, a first sample stored in the sample storage unit 3 is extruded by the syringe 1 to supply the measuring unit of the flow cell 11 with the sample. In the present embodiment, by switching the four-way switching valve 6, serving as a channel switching means, the connection state of the channel can be switched between a first mode and a second mode. The first mode is a state as shown in FIG. 1, in which the first sample storage unit 3 is connected to the sample supply tube 20, and the second sample storage unit 4 is connected to the sample aspiration tube 5. The second mode, to be described later, is a state in which the first sample storage unit 3 is connected to the sample aspiration tube 5, and the second sample storage unit 4 is connected to the sample supply tube 20.

During measurement, the sheath liquid is supplied to the flow cell 11 by an extruding operation of the syringe 12. The sample liquid becomes a narrow flow according to a laminar sheath flow principle. Respective particles of the substance to be inspected within the sample are separated from one another, and pass through the flow unit within the flow cell in a single line. The laser light beam emitted from the laser light source 16 is projected onto this flow, and the optical measurement for the substance to be inspected is thus performed. Measured values are taken in the analysis circuit 23, where the calculation of analysis is performed. Samples after the measurement are sent to the waste liquid receptacle 15, and are stored within the receptacle.

Figure 2:
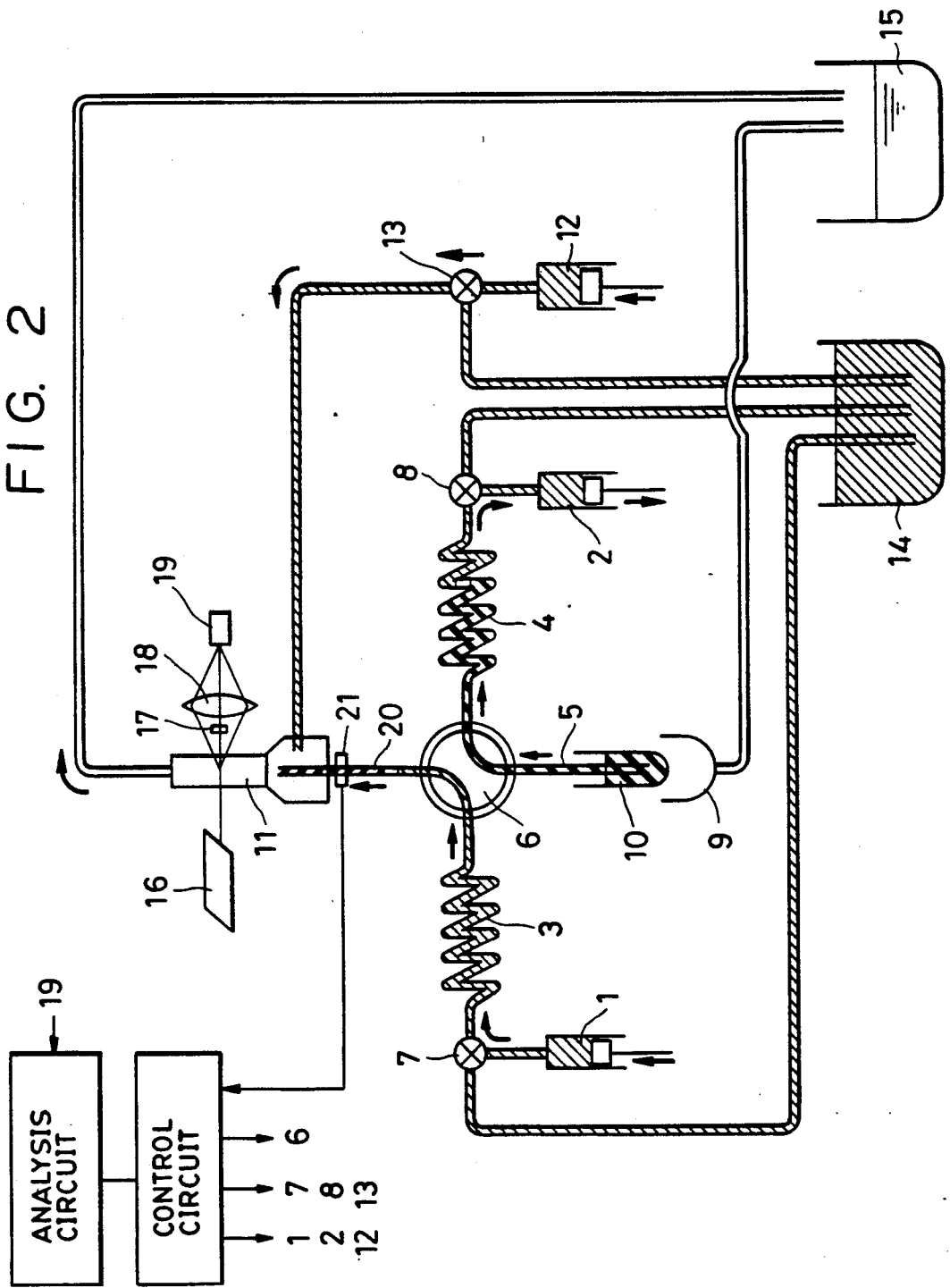
FIGS. 2 through 4 are diagrams for explaining the operation of the embodiment.

FIG. 2 is a diagram in which the syringe 1 supplies the measuring unit with a first sample by its pressurizing operation, and at the same time the syringe 2 aspirates a second sample by its aspirating operation. The second sample has been stored within a sample test tube 10 mounted on a sample aspirating portion. The second sample is aspirated via the sample aspiration tube 5 immersed in the sample test tube 10, and is stored within the sample storage unit 4. It is to be noted that there exists an air layer at the boundary between the sheath liquid and the sample so that the sheath liquid and the sample are not mixed with each other. This can be achieved by performing a slight aspirating operation by the syringe 2 before the sample test tube 10 is set, to aspirate air within a distal end-portion of the sample aspiration tube 5, shown in FIG. 1.

When the sample has passed and subsequently the air layer has passed within the supply the supply tube 20, the air layer is detected by the optical sensor unit 21, and the end of sample supply is determined by a signal from the optical sensor unit 21. It is also possible to determine the passage of the air layer according to an output from the photodetector 19 for measuring the sample. Hence, the end of the sample supply may also be determined according to the output from the photodetector 19. Furthermore, the number of fine particles within the sample may be counted by a counter every time a particle is measured, and the taking-in operation of the sample may be stopped if a predetermined number of particles has been taken in.

After the measurement for the first sample has thus ended, the inside of the flow channel is washed by a sheath liquid flow following immediately after the air layer. The entire inside portion from the sample storage unit 3 to the flow unit of the flow cell 11 is thereby washed by the sheath liquid. After the washing operation has been performed by flowing a predetermined amount of the sheath liquid, the washing operation is terminated. Subsequently, after the storage of the second sample has been completed, the four-way switching valve 6 is rotated by 90 degrees in the counterclockwise direction to switch the flow channel, and the mode shifts from the first mode to the second mode.

Figure 3:
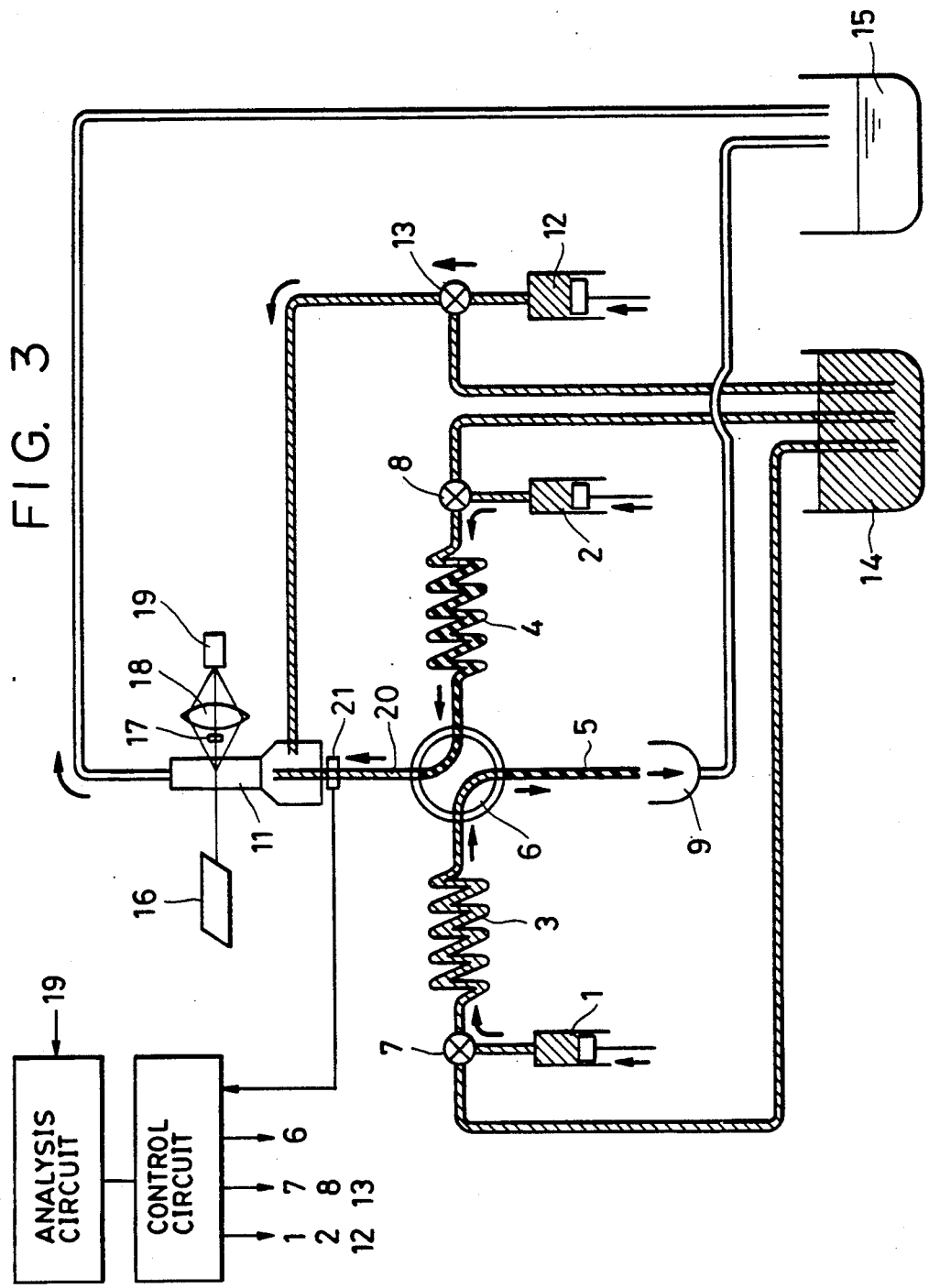

FIG. 3 is a diagram in which the flow channel is switched by the four-way switching valve 6 to provide a second mode, and the supply of the second sample is started by an extruding operation of the syringe 2. Respective particles of the substance to be measured included within the second sample flowing within the flow cell 11 are subjected to optical meaurement, and are sent to the waste liquid receptacle 15 after the measurement has ended. At the same time, the syringe 1 causes the sheath liquid to flow in reverse through the sample aspiration tube 5 by its extruding operation to wash the inside of the tube 5. The waste liquid after flowing in reverse within the sample aspiration tube 5 is received by the saucer 9, and is sent to the waste liquid receptacle 15.

Figure 4:
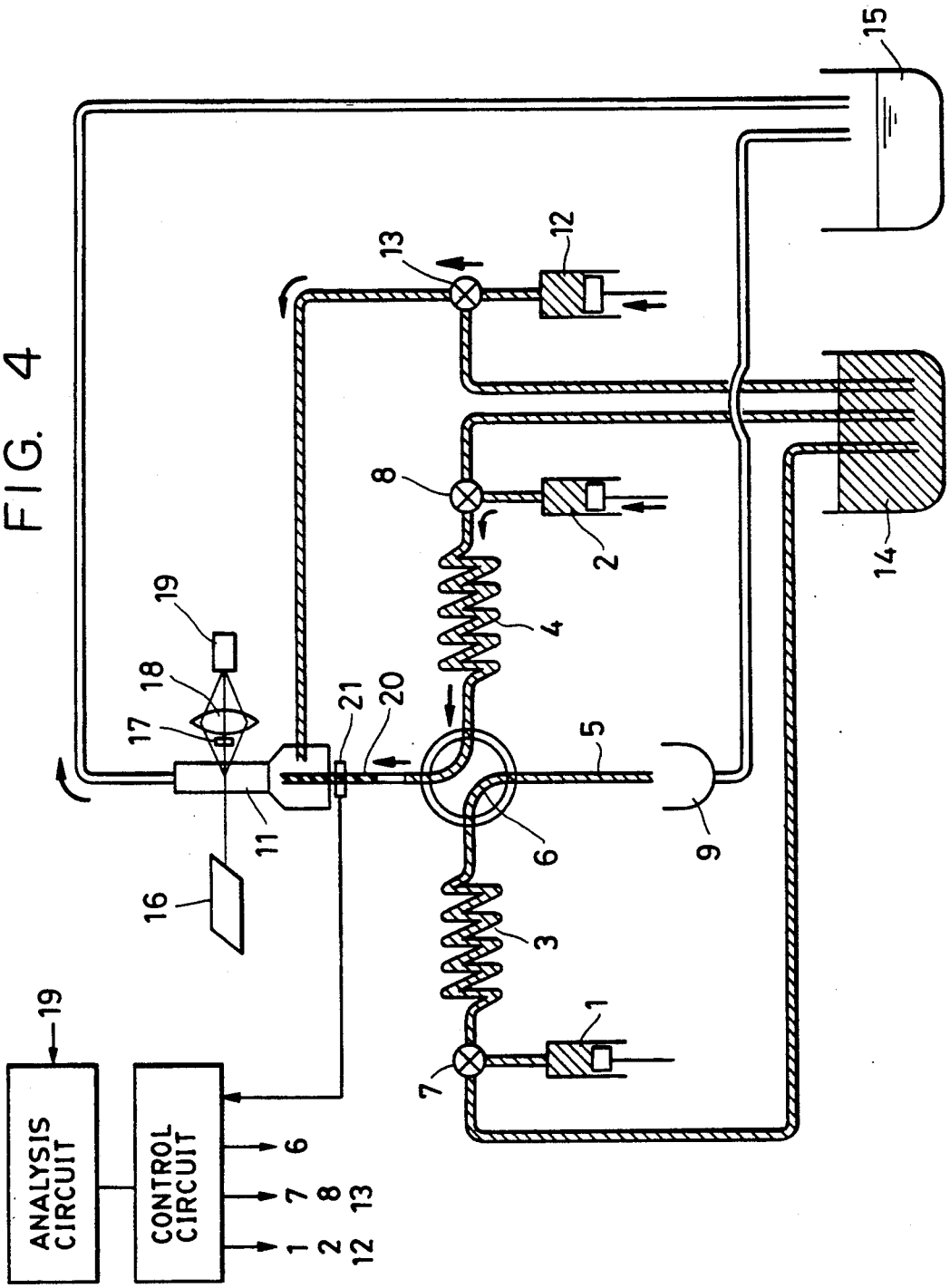

FIG. 4 is a diagram showing a state in which the measurement for the second sample has proceeded in the second mode, and the washing of the sample aspiration tube 5 has ended. Subsequently, a sample test tube containing a third sample is mounted on the sample aspirating portion, and the third sample is stored in the sample storage unit 3 by an aspirating operation of the syringe 1. Furthermore, the flow cell unit is washed by the sheath liquid flowing immediately after the second sample to be sent to the flow cell 11.

Subsequently, the mode is switched again to the first mode, and the measurement is repeated in the same manner.

Figure 5:
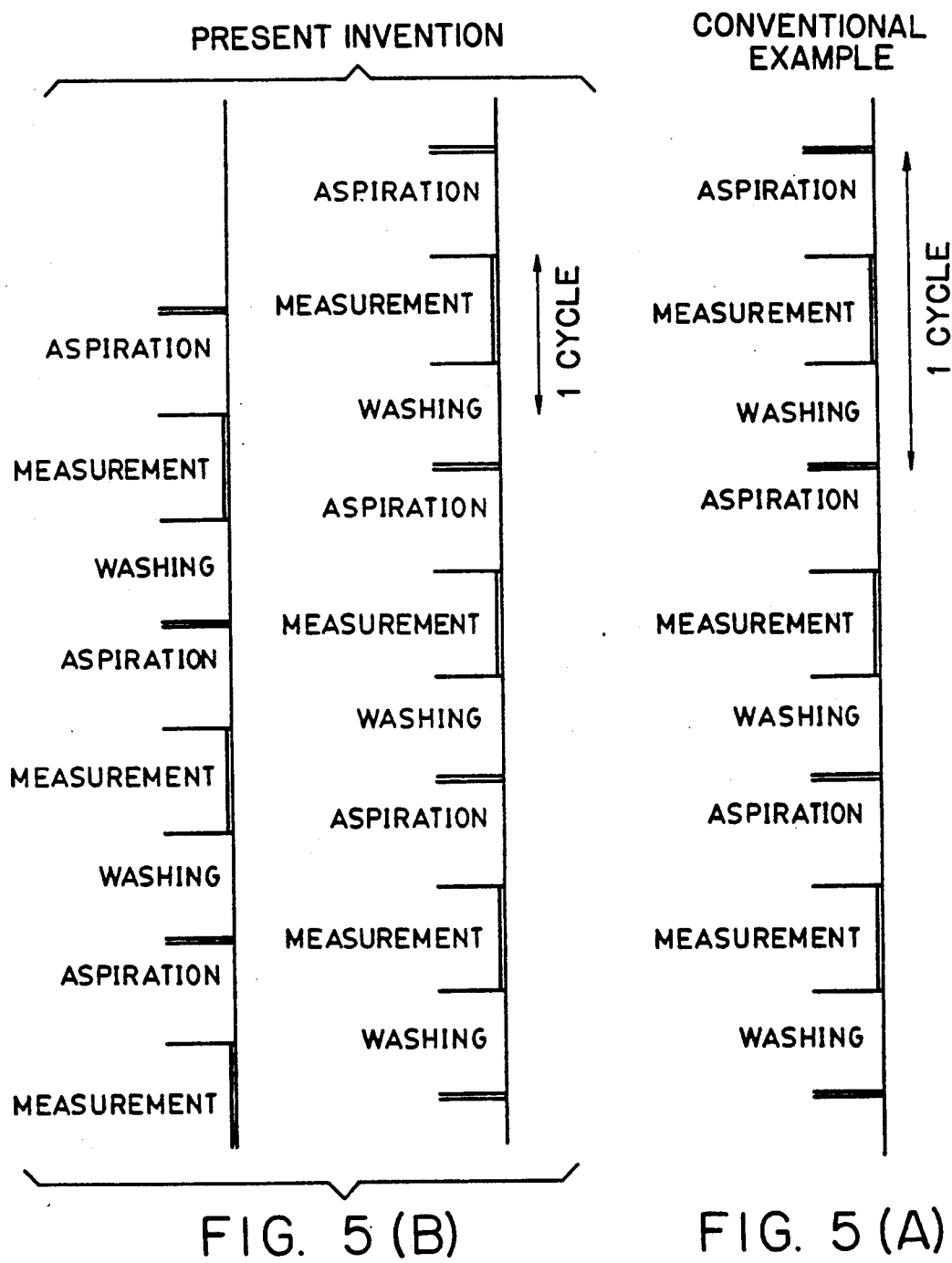
FIG. 5(A) is a time chart of measurement in a conventional example.
FIG. 5(B) is a time chart of measurement in the present invention.

As described above, by repeating the operation of measurement switching between the first mode and the second mode according to commands from the control circuit 22, a plurality of sample liquids are successively measured. A series of these operations are represented by a time chart shown in FIG. 5(B). According to the time chart, it can be understood that it is possible to shorten a cycle for measurement by performing the aspiration and/or washing operation in another mode while a sample is supplied in one mode, and the processing capability is improved when a plurality of samples are continuously measured. This feature provides the apparatus according to the present invention with an efficiency about twice that in a conventional example.

In such operations, only a single laser light source and optical system for measurement are needed as in the prior art, and so the cost and size of the inventive apparatus are nearly identical to those of conventional apparatus.

Figure 6:
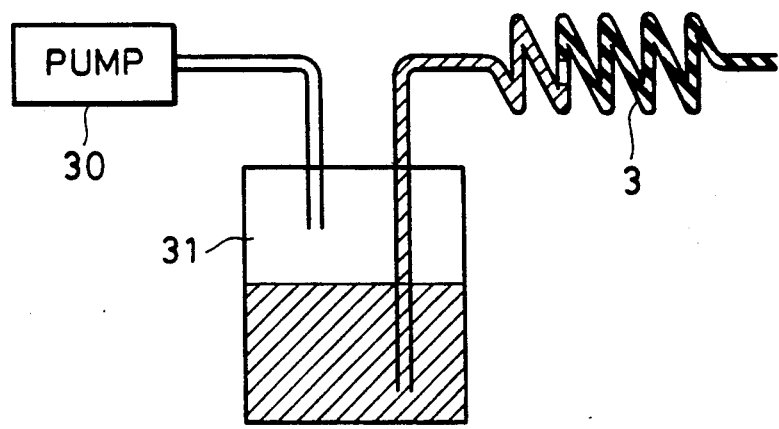
FIG. 6 is a diagram showing the configuration of a different type of pressurizing means.

Although, in the above-described embodiments, the syringes 1 and 2 are used as pressurizing means for performing the extruding and aspirating operation of the sample liquid, the liquid may be extruded and aspirated by controlling air pressure within a closed receptacle in a configuration as shown in FIG. 6. In FIG. 6, a pump 30 capable of performing the pressurizing and aspirating operations controls air pressure within a receptacle 31 filled with a sheath liquid. That is, the sheath liquid is extruded to the sample storage unit 3 by pressurizing the inside of the receptacle 31, and the sheath liquid is aspirated from the sample storage unit 3 by reducing the pressure within the receptacle 31. The configuration is the same for the system of the sample storage unit 4.

Figure 7:
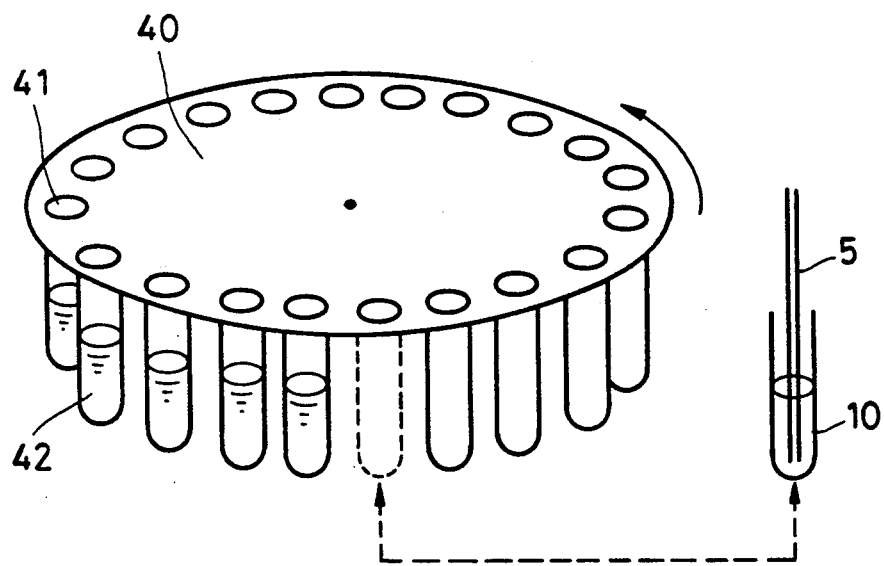
FIG. 7 is a diagram showing the configuration of an autosampler mechanism.

When the sample test tube 10 is mounted on the sample aspiration tube 5, the operator may mount the sample test tube 5 every time the tube is mounted. However, if an autosampler mechanism as illustrated in FIG. 7 is provided to successively and serially supply a plurality of samples, and a mechanical automatic mounting operation is thereby performed, it is possible to further increase efficiency when a large amount of samples are measured. In FIG. 7, a large number of test tube mounting portions 41 are provided along the direction of the outer circumference of a rotating turret 40, and sample test tubes 42 containing sample liquids are mounted thereon. A test tube is drawn out from a predetermined portion of the turret, 40 and is moved to the position of the sample aspiration tube 5 by a mechanism (not shown) as shown by a broken line. After the sample liquid has been aspirated within the apparatus from the sample aspiration tube 5, the vacant test tube is returned to its original position on the turret 40. The turret 40 then rotates by one step, and the next test tube is processed in the same manner.

What is claimed is:

1. A sample supply device comprising:
   a sample receiving channel for receiving a plurality of samples from a source;
   a sample supply channel for supplying the samples to a position to be supplied;
   first and second sample storage means for storing respective samples;
   first and second pressurizing means, in communication with said first and second sample storage means, respectively, for extruding and aspirating samples stored in said first and second storage means; and
   channel switching means capable of switching between a first mode and a second mode, with the first mode being a state in which said first sample storage means is connected to said sample supply channel and said second sample storage means is connected to said sample receiving channel, and the second mode being a state in which said first sample storage means is connected to said sample receiving channel and said second sample storage means is connected to said sample supply channel.

2. A sample supply device according to claim 1, further comprising control means for controlling said channel switching means so as to switch between the first mode and the second mode, and for controlling said first and second pressurizing means so as to receive a sample from said sample receiving channel, store the sample in said second sample storage means, and supply the supply unit with a sample stored in said first sample storage means via said sample supply channel in the first mode, and to receive a sample from said sample receiving channel, store a sample in said first sample storage means, and supply the supply unit with the sample stored in said second sample storage means in the second mode.

3. A sample supply device according to claim 1, further comprising auto-sampler means for serially supplying said receiving channel with a plurality of samples.

4. A sample supply device according to claim 1, wherein each said pressurizing means includes a syringe.

5. A sample supply device according to claim 1, wherein said channel switching means includes a switching valve.

6. A sample supply device according to claim 5, wherein said switching valve comprises a four-way switching valve.

7. A sample supply device according to claim 1, further comprising means for washing said sample receiving channel before or after a sample is received therein.

8. A sample supply device according to claim 7, wherein said washing means causes a washing liquid to flow in reverse through said sample receiving channel.

9. A sample supply device according to claim 1, further comprising means for washing said sample supply channel by flowing a washing liquid therethrough substantially immediately after the sample flows through said sample supply channel.

10. A sample supply device comprising:
first and second sample supply means for independently receiving samples via a common sample receiving channel and for supplying the sample to a position to be supplied; and
control means for controlling said supply means so that said second sample supply means can either receive a sample from said sample receiving channel or wash said sample receiving channel while said first sample supply means supplies the sample to the position to be supplied.

11. A sample supply device according to claim 10, wherein said first and second sample supply means include first and second sample storage means, respectively, for storing predetermined amounts of the respective samples received from said sample receiving channel.

12. A sample supply device according to claim 10, wherein said first and second sample supply means include a common channel for supplying samples to the supply position to be supplied.

13. A sample inspection apparatus comprising:
a sample receiving channel for receiving a plurality of samples from a source;
a sample supply channel for supplying the samples to an inspection position;
first and second sample storage means for storing respective samples;
first and second pressurizing means in communication with said first and second sample storage means, respectively, for extruding and aspirating samples stored in said first and second storage means;
channel switching means capable of switching between a first mode and a second mode, with the first mode being a state in which said first sample storage means is connected to said sample supply channel and said second sample storage means is connected to said sample receiving channel, and the second mode being a state in which said first sample storage means is connected to said sample receiving channel and said second sample storage means is connected to said sample supply channel; and
inspection means for inspecting the sample supplied to the inspection position by said sample supply channel.

14. A sample inspection apparatus according to claim 13, further comprising control means for controlling said channel switching means so as to switch between the first mode and the second mode, and for controlling said first and second pressurizing means so as to receive a sample from said sample receiving channel, store the sample in said second sample storage means, and supply the supply unit with the sample stored in said first sample storage means via said sample supply channel in the first mode, and to receive a sample from said sample receiving channel, store the sample in said first sample storage means, and supply the supply unit with the sample stored in said second sample storage means in the second mode.

15. A sample inspection apparatus according to claim 13, further comprising auto-sampler means for serially supplying said sample receiving channel with a plurality of samples.

16. A sample inspection apparatus according to claim 13, wherein each said pressurizing means includes a syringe.

17. A sample inspection apparatus according to claim 13, wherein said channel switching means includes a switching valve.

18. A sample inspection apparatus according to claim 13, wherein said switching valve comprises a four-way switching valve.

19. A sample inspection apparatus according to claim 13, further comprising means for washing said sample receiving channel before or after a sample is received therein.

20. A sample inspection apparatus according to claim 19, wherein said washing means causes a washing liquid to flow in reverse through said sample receiving channel.

21. A sample inspection apparatus according to claim 13, further comprising means for washing said sample supply channel by flowing a washing liquid therethrough substantially immediately after the sample flows within said sample supply channel.

22. A sample inspection apparatus according to claim 13, wherein said inspection means includes means for optically inspecting the sample.

23. A sample inspection apparatus according to claim 22, wherein said inspection means includes light irradiating means for irradiating light for measurement upon the sample at the inspection position, and measuring means for measuring optical reactions by the sample.

24. A sample inspection apparatus according to claim 23, wherein said light irradiating means includes a laser light source.

25. A sample inspection apparatus comprising:
first and second sample supply means for independently receiving samples via a commom sample receiving channel and for supplying the samples to an inspection position;
control means for controlling said supply means so that said second sample supply means can either receive a sample from said sample receiving channel or clean said sample receiving channel while said first sample supply means supplies the sample to the inspection position; and
inspection means for inspecting the sample supplied at the inspection position.

26. A sample inspection apparatus according to claim 25, wherein said inspection means includes means for optically inspecting the sample.

27. A sample inspection apparatus according to claim 25, wherein said sample supply means include first and second sample storage means, respectively, for storing the samples received via said sample receiving channel.

28. A sample inspection apparatus according to claim 25, wherein the samples are supplied to the inspection position via a common supply channel.

29. A sample supply device according to claim 1, wherein the samples contain fine particles.

30. A sample supply device according to claim 10, wherein the samples contain fine particles.

31. A sample inspection apparatus according to claim 13, wherein the samples contain fine particles and the particles are inspected.

32. A sample inspection apparatus according to claim 25, wherein the samples contain fine particles and the particles are inspected.

* * * * *

UNITED STATES PATENT AND TRADEMARK OFFICE
CERTIFICATE OF CORRECTION

PATENT NO. : 5,182,617

DATED : January 26, 1993

INVENTOR(S) : Yoshito Yoneyama, et al.

It is certified that error appears in the above-identified patent and that said Letters Patent is hereby corrected as shown below:

COLUMN 4:

Line 53, "the supply" (second occurrence) should be deleted.

Signed and Sealed this

Eleventh Day of January, 1994

Attest:

BRUCE LEHMAN

Attesting Officer   Commissioner of Patents and Trademarks